(12) United States Patent
Kiss

(10) Patent No.: US 7,557,081 B2
(45) Date of Patent: Jul. 7, 2009

(54) ALPHA-1-ACID GLYCOPROTEIN FOR THE TREATMENT OF DIABETES

(75) Inventor: Zoltan Kiss, Austin, MN (US)

(73) Assignee: Essential SkinCare, LLC, Austin, MN (US)

( * ) Notice: Subject to any disclaimer, the term of this patent is extended or adjusted under 35 U.S.C. 154(b) by 85 days.

(21) Appl. No.: 11/568,926

(22) PCT Filed: May 27, 2005

(86) PCT No.: PCT/US2005/018749

§ 371 (c)(1),
(2), (4) Date: Nov. 10, 2006

(87) PCT Pub. No.: WO2005/117937

PCT Pub. Date: Dec. 15, 2005

(65) Prior Publication Data

US 2007/0299002 A1   Dec. 27, 2007

Related U.S. Application Data

(60) Provisional application No. 60/574,738, filed on May 27, 2004.

(51) Int. Cl.
*A61K 38/00* (2006.01)
*C12Q 1/54* (2006.01)
(52) U.S. Cl. ............... 514/2; 530/300; 435/14; 514/3
(58) Field of Classification Search ............ None
See application file for complete search history.

(56) References Cited

U.S. PATENT DOCUMENTS

| | | | |
|---|---|---|---|
| 7,048,914 B2 | 5/2006 | Kiss | |
| 2002/0025975 A1 | 2/2002 | Nag et al. | |
| 2002/0107175 A1* | 8/2002 | Wahren et al. | 514/2 |
| 2004/0029175 A1 | 2/2004 | Comper et al. | |
| 2006/0034818 A1 | 2/2006 | Kiss | |
| 2007/0149440 A1 | 6/2007 | Kiss | |

FOREIGN PATENT DOCUMENTS

WO   2005/055956   6/2005

OTHER PUBLICATIONS

Ebeling, et al., 1999, Diabetologia, 42, 1433-1438.*
Dente, et al., 1985, Nucleic acid research, 13, 3941-3952.*
[Retrieved from] "http://web.archive.org/web/20031015080610/http://lpi.oregonstate.edu/infocenter/foods/grains/gigl.html", 2003, 5 pages.*
Zimmet et al., "Global and societal implications of the diabetes epidemic," Nature, vol. 414, pp. 782-787, Dec. 2001.
Saltiel et al., "Insulin signalling and the regulation of glucose and lipid metabolism," Nature, vol. 414, pp. 799-806, Dec. 2001.
Temelkova-Kurktschiev et al., "Subclinical Inflammation is Strongly Related to Insulin Resistance but not to Impaired Insulin Secretion in a High Risk Population for Diabetes," Metabolism, vol. 51, No. 6, pp. 743-749, Jun. 2002.
Duncan et al., "Low-grade Systemic Inflammation and the Development of Type 2 Diabetes," Diabetes, vol. 52, pp. 1799-1805, Jul. 2003.
McMillan, "Increased Levels of Acute-Phase Serum Proteins in Diabetes," Metabolism, vol. 38, No. 11, pp. 1042-1046, 1989.
Spranger et al., "Inflammatory Cytokines and the Risk to Develop Type 2 Diabetes," Diabetes, vol. 52, pp. 812-817, Mar. 2003.
Hu et al., "Inflammatory Markers and Risk of Developing Type 2 Diabetes in Women," Diabetes, vol. 53, pp. 693-700, Mar. 2004.
Fournier et al., "Alpha-1-acid glycoprotein," Biochim. Biophys. Acta, vol. 1482, pp. 157-171, 2000.
Engstrom et al., "Incidence of Fatal or Repaired Abdominal Aortic Aneurysm in Relation to Inflammation-sensitive Plasma Proteins," Arterioscler. Throm. Vasc. Biol., vol. 24, pp. 337-341, 2004.
Lind et al., "Risk of Myocardial Infarction and Stroke in Smokers is Related to Plasma Levels of Inflammation-sensitive Proteins," Arterioscler. Throm. Vasc. Biol., vol. 24, pp. 577-582, 2004.
Snyder et al., "Inhibition of Platelet Aggregation by $\alpha$1-acid Glycoprotein," Arch. Intern. Med., vol. 136, pp. 778-781, Jul. 1976.
Liebert et al., "Protection by $\alpha$1-acid glycoprotein against tumor necrosis factor-induced lethality," J. Exp. Med., 180, 1571-1575,1994.
Van Molle et al., "$\alpha$1-acid glycoprotein and $\alpha$1-antitrypsin inhibit TNF-induced but not anti-fas-induced apoptosis of hepatocytes in mice," J. Immunol., 159, 3555-3564, 1997.
Williams et al., "$\alpha$1-acid glycoprotein reduces local and remote injuries after intestinal ischemia in the rat," Am. J. Physiol., 36, G1031-G1035, 1997.
Muchitsch et al., "Effects of $\alpha$1-acid glycoprotein in different models of shock," Fundam. Clin. Pharmacol., 12, 173-181, 1998.
Moore et al., "Alpha-1-acid (AAG, orosomucoid) glycoprotein: Interaction with bacterial lipopolysaccharide and protein from sepsis," Inflammation, 21, 69-82, 1997.
Curry et al., "Modulation of microvessel wall charge by plasma glycoprotein orosomucoid," Am. J. Physiol., 257, H1354-H1359,1989.

(Continued)

*Primary Examiner*—Cecilia Tsang
*Assistant Examiner*—Satyanarayana R Gudibande
(74) *Attorney, Agent, or Firm*—Faegre & Benson LLP

(57) ABSTRACT

Methods of using alpha-1-acid glycoprotein, or an active derivative, to modulate the blood glucose level in mammals, particularly humans, is described. A therapeutically effective amount of alpha-1-acid glycoprotein is administered to a patient afflicted with Type 1 or Type 2 diabetes to lower the blood glucose level. An anti-diabetic medicament, particularly insulin, may also be administered in combination with alpha-1-acid glycoprotein. The invention also provides a treatment regimen by periodically administering alpha-1-acid glycoprotein and further provides a method of mitigating the inhibitory effect of an acute phase protein on the action of insulin. Finally, the invention provides for the use of alpha-1-acid glycoprotein or an active derivative for the manufacture of a medicament for the treatment of diabetes, for the manufacture of a medicament for mitigating the hyperglycemic effect of an acute phase protein, or for the manufacture of a medicament for the treatment of chronic or sub-chronic inflammation.

14 Claims, No Drawings

OTHER PUBLICATIONS

Rolin et al., "The long-acting GLP-1 derivative NN2211 ameliorates glycemia and increases cell mass in diabetic mice," Am. J. Physiol. Endocrinol. Metab., 283, E745-E752, 2002.

Mason et al., "Pulmonary Cell Biology," Am. J. Resp. Crit. Care Med., 157, S72-S81, 1998.

Giannoukakis et al., "Gene therapy technology applied to disorders of glucose metabolism: Promise, achievements, and prospects," Biotechniques, 35, 122-145, 2003.

Costello et al., "Inhibition of platelet aggregation by native and desialised alpha-1 acid glycoprotein," Nature, 281, 677-678, 1979.

* cited by examiner

ALPHA-1-ACID GLYCOPROTEIN FOR THE TREATMENT OF DIABETES

This application claims priority from PCT Application No. PCT/US2005/018749, filed May 27, 2005, now Publication No. WO 2005/117937, which claims the benefit of provisional application Ser. No. 60/574,738, filed May 27, 2004, now expired.

TECHNICAL FIELD

Mainly due to decreased physical activity and increased food consumption, an increasing number of people are becoming overweight and obese. The metabolic changes in the obese subjects gradually lead to the desensitization of major tissues (skeletal muscle, adipose tissue, and liver) to the actions of insulin on glucose metabolism resulting in hyperglycemia (high blood glucose levels) and the development of Type 2 (i.e. insulin-independent) diabetes. Recently, there has been an escalation of diabetes, and this trend appears to continue in the foreseeable future. Diabetes already afflicts an estimated 6% of the adult population in Western societies. Its worldwide frequency is projected to grow by 6% per annum potentially reaching a total of 200-300 million cases in 2010 [Zimmet, P., Alberti, K. G. M. and Shaw, J., *Global and societal implications of the diabetes epidemic*, Nature, 414, 782-787 (2001)]. About 90%-95% of all diabetic patients fall into the Type 2 category, while the rest have Type 1 (i.e. insulin-dependent) diabetes. Type 1 diabetes results from an absolute deficiency of insulin due to destruction of insulin-producing β-cell in the islets through an abnormality of the autoimmune system.

Despite large variations in carbohydrate intake with various meals, plasma glucose normally is maintained in a narrow range of 4-6 mM in non-diabetic individuals. This tight control is regulated by the balanced operation of three major mechanisms. These mechanisms are: (i) glucose absorption from the intestine, (ii) glucose production by the liver, and (iii) uptake and metabolism of glucose by the peripheral tissues, mainly the skeletal muscle and fat tissue. In skeletal muscle and fat tissue, insulin increases uptake of glucose as well as conversion of glucose to other metabolites such as glycogen and fat (mainly triglycerides). In the liver, insulin inhibits the release of glucose from glycogen and the synthesis of new glucose [Saltiel, A. R. and Kahn, C. R., *Insulin signaling and the regulation of glucose and lipid metabolism*, Nature, 414, 799-806 (2001)]. In Type 2 diabetes, muscle, fat and liver cells become less sensitive to the actions of insulin. While initially the islets produce and release more insulin to compensate for decreased insulin sensitivity, eventually the insulin secretion system also breaks down.

One of the significant risk factors for developing Type 2 diabetes is inflammation, including sub-chronic inflammation [Temelkova-Kurktschiev, T., Siegert, G., Bergmann, S., Henkel, E., Koehler, C., Jaros, W. and Hanefeld, M., *Subclinical inflammation is strongly related to insulin resistance but not to impaired insulin secretion in a high risk population for diabetes*, Metabolism, 51, 743-749 (2002); Duncan, B. B., Schmidt, M. I., Pankow, J. S., Ballantyne, C. M., Couper, D., Vigo, A., Hoogeveen, R., Folsom, A. R. and Heiss, G., *Low-grade systemic inflammation and the development of Type 2 diabetes*, Diabetes, 52, 1799-1805 (2003)]. Inflammation is accompanied by the synthesis of liver-derived acute phase proteins such as C-reactive protein, $\alpha_1$-antitrypsin (AT), serum amyloid, ceruloplasmin, haptoglobin, fibrinogen, $\alpha_1$-acid glycoprotein (AGP), and $\alpha_1$-antichymotrypsin. Increased levels of most of these acute phase proteins along with increased production of inflammatory cytokines such as tumor necrosis factor, interleukin-1, and interleukin-6, were shown to be correlated with the development of diabetes. [McMillan, D. E., *Increased levels of acute-phase serum proteins in diabetes*, Metabolism, 38, 1042-1046 (1989); Spranger, J., Kroke, A., Mohlig, M., Hoffmann, K., Bergmann, M. M., Ristow, M., Boeing, H. and Pfeiffer, A. F. H., *Inflammatory cytokines and the risk to develop Type 2 diabetes*, Diabetes, 52, 812-817 (2003); Hu, F. B., Meigs, J. B., Li, T. Y., Rifai, N. and Manson, J. E., *Inflammatory markers and risk of developing Type 2 diabetes in women*, Diabetes, 53, 693-700 (2004)].

The most important properties of acute phase protein AGP have been reviewed recently [Fournier, T., Medjoubi-N, N. and Poequet, D., *Alpha-1-acid glycoprotein*, Biochim. Biophys. Acta, 1482, 157-171 (2000)]. AGP is a 41-43 kDa glycoprotein composed of a single chain of 183 amino acids (human) with two disulfide bridges. The carbohydrate content, which is somewhat variable, represents up to 45% of its molecular weight. Its normal range of concentration in the serum is in the range of 0.5-1.0 g/L, which can be increased several-fold in response to inflammation, infection, and systemic tissue injury [Fournier, T., Medjoubi-N, N. and Poequet, D., *Alpha-1-acid glycoprotein*, Biochim. Biophys. Acta, 1482, 157-171 (2000); Engstrom, G., Borner, G., Lindblad, B., Janzon, L. and Lindgarde, F., *Incidence of fatal or repaired abdominal aortic aneurism in relation to inflammation-sensitive proteins*, Arterioscler. Throm. Vasc. Biol., 24, 337-341 (2004); Lind, P., Engstrom, G., Stavenow, L., Janzon, L., Lindgarde, F. and Hedblad, B., *Risk of myocardial infarction and stroke in smokers is related to plasma levels of inflammation-sensitive proteins*, Arterioscler. Throm. Vasc. Biol., 24, 577-582 (2004)].

AGP has been shown to exert several positive physiological effects. Perhaps the most important is its ability to inhibit platelet aggregation which should potentially decrease cardiovascular risk [Snyder, S. and Coodley, E. L., *Inhibition of platelet aggregation by $\alpha_1$-acid glycoprotein*, Arch. Intern. Med., 136, 778-781 (1976); Costello, M., Fiedel, B. A. and Gewurz, H., *Inhibition of platelet aggregation by native and desialised alpha-1 acid glycoprotein*, Nature, 281, 677-678 (1979)]. Other useful physiological effects include protection against (i) tumor necrosis factor-induced lethality [Liebert, C., Brouckaert, P. and Fiers, W., *Protection by $\alpha_1$-acid glycoprotein against tumor necrosis factor-induced lethality*, J. Exp. Med., 180, 1571-1575 (1994)] and (ii) cell death [Molle, W. V., Libert, C., Fiers, W. and Brouckaert, P., *$\alpha_1$-acid glycoprotein and $\alpha_1$-antitrypsin inhibit TNF-induced but not anti-fas-induced apoptosis of hepatocytes in mice*, J. Immunol., 159, 3555-3564 (1997)], (iii) injuries after intestinal ischemia [Williams, L. P., Weiser, M. R., Pechet, T. T. V., Kobzik, L., Moore, F. D. and Hechtman, H. B., *$\alpha_1$-acid glycoprotein reduces local and remote injuries after intestinal ischemia in the rat*, Am. J. Physiol., 36, G1031-G1035 (1997)], and (iv) various types of shocks [Muchitsch, E-M., Auer, W. and Pichler, L., *Effects of $\alpha_1$-acid glycoprotein in different models of shock*, Fundam. Clin. Pharmacol., 12, 173-181 (1998); Moore, D. F., Rosenfeld, M. R., Gribbon, P. M., Winlove, C. P. and Tsai, C. M., *Alpha-1-acid (AAG, orosomucoid) glycoprotein: Interaction with bacterial lipopolysaccharide and protein from sepsis*, Inflammation, 21, 69-82 (1997)] probably by maintaining capillary permeability by decreasing the polyanionic charge selectivity of the endothelial barrier [Curry, F. E., Rutledge, J. C. and Lenz, J. F., *Modulation of microvessel wall charge by plasma glycoprotein orosomucoid*, Am. J. Physiol., 257, H1354-H1359 (1989)].

SUMMARY OF THE INVENTION

The present invention generally provides a method of controlling or stabilizing abnormally elevated levels of blood glucose in mammals, particularly humans, by administering $\alpha_1$-acid glycoprotein (AGP) or an active derivative of $\alpha_1$-acid glycoprotein. The terms "$\alpha_1$-acid glycoprotein" and "AGP" refer to the related group of glycosylated or non-glycosylated $\alpha_1$-acid glycoprotein core proteins or fragments that are capable of lowering blood glucose level. The phrase "active derivative" refers to any of the glycosylated or non-glycosylated AGP-like core proteins or fragments that are capable of lowering blood glucose level. The term "abnormally elevated" refers to a human's blood glucose level that is higher than the normal range of about 4-6 mM.

In one embodiment, the invention provides a method of reducing the blood glucose level in a mammal by administering a therapeutically effective amount of AGP, or an active derivative. The method may also include the step of administering an anti-diabetic medicament in combination with the AGP or active derivative. The phrase "in combination" refers to the use of an anti-diabetic medicament that may be administered simultaneously or separately from administration of the AGP or active derivative. The phrase "therapeutically effective amount" is used throughout this application to indicate a dosage that is effective in, or is targeted at, attaining or maintaining a level of glucose in a mammal's blood that is within the normal range for that mammal. A range of normal blood glucose level in a human is about 4-6 mM. A therapeutically effective amount of AGP may inhibit hyperglycemic effect of an acute phase protein without compromising the basic physiological function of the remaining active acute phase proteins. A therapeutically effective amount of AGP may also enhance the glucose-lowering effect of insulin.

In another embodiment, the invention also provides a method of reducing the blood glucose level in a mammal by identifying a mammal with an above-normal blood level of an acute phase protein and administering to the mammal a therapeutically effective amount of AGP, or an active derivative. The term "acute phase protein" refers to liver-derived proteins or protein fragments that are synthesized in increased quantities during inflammation, including chronic and sub-chronic inflammation. Examples of acute phase proteins include C-reactive proteins (CRP), $\alpha_1$-antitrypsin (AT), serum amyloid, ceruloplasmin (CP), haptoglobin, fibrinogen, and $\alpha_1$-antichymotrypsin. The term "above-normal" refers to an amount of at least one acute phase protein that indicates chronic or sub-chronic inflammation in the mammal. The step of identifying a mammal with an above-normal blood level of an acute phase protein described here may be performed in all embodiments of the invention. There are several suitable methods available for identifying mammals with an above-normal level of an acute phase protein. Generally, venous blood is drawn from the mammal. A radial immunodiffusion method can then be used to quantitatively analyze the amount of AGP, $\alpha_1$-antitrypsin, $\alpha_2$-macroglobulin, ceruloplasmin, or haptoglobin in the sample of blood. One example of a suitable commercially available radial immunodiffusion method is available from Behring Diagnostics (Mannheim, Germany). The level of C-reactive protein may be determined by an immunological agglutination test or by the single radial immunodiffusion method. An example of a suitable commercially available immunological agglutination test is available from Boehringer Mannheim (Mannheim, Germany) and an example of a suitable single radial immunodiffusion method is available from Eiken Co. (Osaka, Japan). Finally, the concentration of active plasminogen activator inhibitor-1 antigen can be determined using commercially available enzyme immunoassay, such as, for example, one available from Immuno AG, (Heidelberg, Germany).

In yet another embodiment, the invention provides a treatment regimen for treating diabetes by periodically administering a therapeutically effective amount of AGP, or an active derivative. The term "periodically" refers to repeated administration of AGP aimed at restoring or maintaining a normal level of glucose in the human's blood. The periods do not have to be uniform, although they could be. For example, the treatment regimen could include the administration of AGP about once per week, about twice per week, or about once every 48 hours. The treatment regimen may be effective to maintain the human's blood glucose level below about 10 mM, more suitably below 8mM. The treatment regimen may be effective to maintain the human's blood glucose level within the more normal range of 4 mM to 6 mM. The therapeutically effective amount of AGP may be different at each administration depending upon the amount of glucose in the human or on the rate of glycosylation or size of the protein. This treatment regimen may be used to treat both Type 1 and Type 2 diabetic mammals, including humans.

In still another embodiment, the invention provides a treatment regimen for treating chronic or sub-chronic inflammation by periodically administering a therapeutically effective amount of AGP, or an active derivative. As with the treatment regimen for treating diabetes, the term "periodically" refers to repeated administration of AGP aimed at restoring or maintaining a normal level of glucose in the human's blood. The periods do not have to be uniform, although they could be. The treatment regimen may be effective to maintain the human's blood glucose level below about 10 mM, more suitably below 8mM. The treatment regimen may be effective to maintain the human's blood glucose level within the more normal range of 4 mM to 6 mM.

In all of the embodiments, the method or treatment regimen may also include the step of administering an anti-diabetic medicament in combination with the AGP or active derivative. Examples of suitable anti-diabetic medicaments include insulin secretogogue, a biguanide, an inhibitor of $\alpha$-glucosidase, a thiazolidinedione, or NN2211.

In other embodiments, the invention provides for the use of AGP, or an active derivative, for manufacture of a medicament. In one embodiment, the medicament is used for the treatment of diabetes. In another embodiment, the medicament is used to reduce the hyperglycemic effect of an acute phase protein. In still another embodiment, the medicament is used for the treatment of chronic or sub-chronic inflammation. The medicament used in each of these embodiments may comprise AGP or an active derivative dissolved or dispersed in a suitable carrier. Furthermore, the medicament used in each of these embodiments may be suitable for coadministration with an anti-diabetic medicament, such as those described above.

DETAILED DESCRIPTION OF THE INVENTION

It has been observed that AGP that is naturally found in mammals, also known as orosomucoid, significantly reduces the rise in blood glucose level in mice in standard glucose tolerance tests. AGP, isolated from either human or bovine blood, when administered to mice is similarly effective at reducing the rise in blood glucose in standard glucose tolerance tests. AGP is also able to prevent the glucose-enhancing effect of acute phase proteins, particularly ceruloplasmin, while not affecting the glucose-lowering effects of insulin. Since AGP does not exert any known major toxic effects, these findings indicate that AGP will be useful to lower blood glucose level in both Type 1 and Type 2 diabetic patients.

AGP maintains its glucose-stabilizing effect over at least a 27 hour period without observing signs of hypoglycemia, longer than the glucose-stabilizing effect of insulin. Since the half-life time of AGP in the circulation is several days, it is reasonable to assume that the effect of AGP will remain for several days. Therefore, it is expected that, in contrast to insulin, much less frequent treatments with AGP will be sufficient to maintain glycemic control.

AGP also significantly lowered the greatly enhanced blood glucose level in streptozotocin-treated mice. Since streptozotocin acts by selectively inducing the death of insulin-producing islet β-cells, streptozotocin-treated animals are often used as models of Type 1 diabetes. Thus, another potential application of AGP is to use it to lower blood glucose level in Type 1 diabetic humans.

The mechanism by which inflammation affects insulin sensitivity is presently not clear. One possibility is that acute phase proteins, or at least one acute phase protein, are capable of reducing the glucose-stabilizing effects of insulin and/or increasing blood glucose levels on their own. It is thought that other acute phase proteins can at least partially counter-act these effects. To test this theory, acute phase proteins such as fibrinogen, ceruloplasmin (CP), C-reactive proteins (CRP), haptoglobin, $\alpha_1$-antitrypsin (AT) and AGP were injected into mice intraperitoneally 24 hours before performing glucose tolerance tests on these mice. It was shown that the acute phase proteins fibrinogen and AGP significantly decreased blood glucose levels. While AGP inhibits platelet aggregation, and therefore can help to prevent artery blockage, excess fibrinogen can lead to blood coagulation and therefore artery blockage and heart failure. Accordingly, the present invention focuses only on the glucose-lowering effect of AGP in relation to the effects of endogenous insulin, exogenous insulin, and exogenous acute phase proteins. The other tested acute phase proteins did not exhibit the glucose-reducing effect shown by fibrinogen and AGP. Haptoglobin had no glucose-stabilizing effect while CP, CRP and AT actually elevated blood glucose levels, both in the absence and presence of insulin. AGP might also be useful to treat diabetic patients by aiding the hypoglycemic effect of insulin and by preventing the blood glucose-enhancing effects of other acute phase proteins.

Alterations in a mammal's physiology can lead to decreased insulin sensitivity or reduced insulin production, or both, leading to elevated levels of blood glucose and diabetes. One common alteration in physiology that may lead to decreased insulin sensitivity and reduced insulin production is inflammation, particularly chronic or sub-chronic inflammation. Inflammation is usually accompanied by an increase in acute phase proteins in the blood. Therefore, it is thought that some of the acute phase proteins, including ceruloplasmin (CP), $\alpha_1$-antitrypsin, and C-reactive protein (CRP), may contribute to the enhanced blood glucose levels.

To test this theory, AGP was administered to mice to determine the effect of AGP on blood glucose levels in the presence and absence of CP, one of the acute phase proteins that is thought to contribute to enhanced blood glucose levels. It was found that AGP prevents the glucose enhancing action of CP, indicating that AGP can effectively prevent the hyperglycemic effects of other acute phase proteins. In mice, AGP also prevented the rapid rise in blood glucose level in the absence of an acute phase protein, indicating that AGP has the ability to prevent hyperglycemia. The glucose-stabilizing effects of AGP were compared to insulin and it was found that AGP had much longer lasting glucose-stabilizing effects. The term "stabilizing" refers to the controlling, maintaining, or decreasing, if needed, of blood glucose levels.

In the glucose tolerance tests performed with mice reported below, AGP effectively prevented sharp rise in the blood glucose level induced by intraperitoneally administered glucose. Even though AGP was administered 24 hours prior to glucose, the glucose-stabilizing effect was maintained over the whole observation period. This indicates that AGP has a long-lasting glucose stabilizing effect. Despite the long pre-treatment with AGP, the mice that had been administered AGP had about the same blood glucose level just before the administration of glucose than mice that had not been administered AGP, strongly suggesting that AGP does not cause hypoglycemia.

The glucose tolerance test is one of the most often used methods to determine whether an agent is capable of increasing or decreasing the blood glucose level. A very large body of evidence in the relevant literature indicates that agents that can alter blood glucose level in mice also can be expected to have similar effects in humans. The finding that AGP, like insulin, is capable of reducing the increase in blood glucose in glucose tolerance tests in mice is a strong indication that AGP is a prospective anti-diabetic agent in humans. The observation that the effect of AGP lasts much longer than that of insulin indicates that for the treatment of diabetic patients less frequent applications of AGP will be sufficient. It was also found that AGP does not interfere with the action of insulin. Therefore, an anti-diabetic medicament may be administered in combination with the administration of AGP, either simultaneously or separately. For example, AGP may be administered once or twice a week to prevent large increases in the blood glucose level. An anti-diabetic medicament may also be administered during AGP treatment if, due to an unusually large glucose load, AGP alone may not be expected to be able to keep the blood glucose level at near normal level. Examples of suitable anti-diabetic medicaments include insulin secretogogue, a biguanide, an inhibitor of aαglucosidase, a thiazolidinedione, or NN2211. For fine-tuning of glucose level in AGP-treated diabetic patients, a recently developed long-acting derivative of glucagon-like peptide-1 (GLP-1), NN2211, or similar derivatives, may be especially useful as the anti-diabetic medicament. NN2211 has the useful property that it enhances insulin secretion by the islet only at higher than normal blood glucose levels [Rolin, B., Larsen, M. O., Gotfredsen, C. F., Deacon, C. F., Carr, R. D., Wilken, M. and Knudsen, L. B., *The long-acting GLP-1 derivative NN2211 ameliorates glycemia and increases β-cell mass in diabetic mice, Am. J. Physiol. Endocrinol. Metab.,* 283, E745-E752 (2002)].

To determine the amount of AGP required to normalize blood glucose level in humans, the following factors should be considered. First, the amounts of AGP required to control blood glucose levels in mice and rats in glucose tolerance test were in the range of 24-40 mg/kg body mass. Second, the high load of glucose administered in the glucose tolerance test (3 g/kg) occurs very rarely, if ever, in humans. Accordingly, it is expected that lower amounts of AGP will be sufficient to provide control in humans. Third, although AGP was administered via intraperitoneal injections in the experiments, AGP could be administered via an intravenous, subcutaneous, or intradermal injection, although intravenous is thought to be the most efficient. In one embodiment, a suitable dose ranges from about 0.1-4 g AGP per 100 kg of body mass depending on the severity of diabetes.

AGP may also be administered via inhalation (aerosol administration) or gene therapy. Methods of administering proteins via aerosol inhalation are known in the art. For example, the methods described in Mason, R. J. and Crystal, R. G., *Pulmonary Cell Biology, Am. J. Resp. Crit. Care Med.*, 157, S72-S81 (1998), which is hereby incorporated by reference, may be used to administer AGP according to the present invention. Various methods of gene therapy technology are also known in the art. For example, the methods reported in Giannoukakis, N. and Trucco, M. *Gene therapy technology applied to disorders of glucose metabolism: Promise, achievements, and prospects, Biotechniques,* 35, 122-145 (2003), hereby incorporated by reference, may be suitable and therefore may be used to administer AGP or a derivative according to the present invention. However, administration of AGP in human diabetic patients via intravenous injection is most suitable.

Depending upon the mode of administration, it may be beneficial to administer the AGP as a preparation of a physiologically acceptable carrier and the AGP or active derivative dissolved or dispersed in the carrier. Since AGP is water-soluble, one example of a suitable carrier is physiological saline (0.9% sodium chloride). Other suitable carriers include sterilized water that may be diluted with Lactated Ringer's solution available from LR, Baxter Healthcare (Deerfield, Ill.), or phosphate buffered saline.

Since AGP is a significantly larger protein than insulin, its distribution to the peripheral glucose metabolizing tissues (skeletal muscle, adipose tissue, liver) probably requires somewhat more time than the distribution of insulin. However, since the half-life time of AGP in the circulation is several days, rather than the relatively short half-life time of insulin of several minutes, AGP will likely to exert its effects for a longer time period compared to insulin. Because of its long-lasting effect, in one embodiment administration of AGP is administered about 24-48 hours prior to the expected glucose load when the exact timing of increased glucose load cannot be predicted. This is significant, because presently available anti-diabetic agents do not provide for long-term protection against large fluctuations in blood glucose level without the danger of producing hypoglycemia.

In another embodiment, AGP could also be administered between 0-24 hours prior to an expected glucose load. As shown in Example 2, administration of human AGP similarly reduced mouse blood glucose levels in glucose tolerance tests when administered 2 hours or 24 hours prior to the glucose load. This strongly indicates that the action of AGP is relatively rapid, even though its action may be less rapid than that of insulin. Therefore, AGP could be used in emergency cases when there is a need to rapidly decrease blood glucose level for a longer time period. For such purpose, AGP may be used alone or in combination with insulin. When used with insulin, AGP should allow the administration of less insulin thereby reducing the danger of hypoglycemia.

In addition, AGP greatly decreased the blood glucose level in mice treated with streptozotocin. Streptozotocin (STZ) is an agent that is used to destroy the insulin-producing β-cells, thereby inducing Type 1 diabetes. Administration of AGP to mice 24 hours prior to STZ resulted in significant reduction in blood glucose level. After nine days of treatment STZ also reduced the body weight of mice by one third while in the simultaneous presence of STZ and AGP the animals did not lose weight. The data indicates that AGP may be used to control blood glucose and normalize body weight in Type 1 diabetic subjects.

In glucose tolerance tests, human AGP not only decreased blood glucose in mice but also in rats. This strongly indicates that the effect of AGP on blood glucose is not specific to mice but most probably occurs in most mammals including humans.

In other embodiments, the invention provides for the use of AGP, or an active derivative, for manufacture of a medicament. In one embodiment, the medicament is used for the treatment of diabetes. In another embodiment, the medicament is used to reduce the hyperglycemic effect of an acute phase protein. In still another embodiment, the medicament is used for the treatment of chronic or sub-chronic inflammation. In another embodiment, the medicament is suitable for co-administration with an anti-diabetic medicament.

The medicament may be manufactured via any suitable standard manufacturing method. For example, the medicament may be formed of AGP or an active derivative dissolved or dispersed in a suitable carrier. AGP may be obtained from various sources. AGP derived from both human and bovine sources were similarly effective in preventing the rise in blood glucose level in mice, as shown in the examples. The homology between the bovine and human cDNA nucleotide sequences is at least 70% but probably not greater than 85%. Thus, AGP from various species with significantly less than full homology to the human protein would be expected to reproduce, at least partially, the effects of bovine and human proteins on blood glucose level. It is also expected that species with smaller, probably common (conservative), cDNA sequences are sufficient to create AGP that is at least as effective as bovine or human derived-AGP. Such conservative regions in the coding sequences of AGP clearly exist [Fournier, T., Medjoubi-N, N. and Poequet, D., *Alpha-1-acid glycoprotein, Biochim. Biophys. Acta,* 1482, 157-171 (2000)].

The effectiveness of AGP may vary based upon its unique glycosylation. AGP molecular species contain various N-linked complex glycans. It has been found that the various glycoforms of AGP have different effects on lymphocyte proliferation and platelet aggregation [Fournier, T., Medjoubi-N, N. and Poequet, D. *Alpha-1-acid glycoprotein, Biochim. Biophys. Acta,* 1482, 157-171 (2000); Pos, O., Oostendorp, R. A. J., Van Der Stelt, M. E., Scheper, R. J. and Van Dijk, W., *Con A-nonreactive human $\alpha_1$-acid glycoprotein (AGP) is more effective in modulation of lymphocyte proliferation than Con A-reactive AGP serum variants, Inflammation,* 14, 133-141 (1990)]. Therefore, it is possible that the various AGP glycoforms may have differing abilities in reducing blood glucose level. However, approximately 12-20 different glycoforms of AGP can be detected in the human plasma, so the extent of micro-heterogeneity in a given preparation may alter the effectiveness.

Highly purified (99% purity) AGP from human, bovine, rat, and sheep blood are commercially available from the Sigma-Aldrich, Inc. (St. Louis, Mo.). A method for the isolation of highly purified AGP has been described [Hao, Y-L. and Wickerhauser, M., *Development of large-scale fractionation methods IV. A simple method for the large-scale preparation of $\alpha_1$-acid glycoprotein, Biochim. Biophys. Acta,* 322, 99-108 (1973)]. AGP as well as AGP-like proteins with similar effects on blood glucose level may be isolated from human blood or tissues, or from the blood or tissues of any mammals.

AGP-like proteins may also be isolated from other animals. It was shown that Euglena *gracilis* cells express a close relative of AGP that is recognized by an antibody produced against the rat form of AGP [Durand, G., Delranc, C., Bonaly, J., Chacun, H., Porquet, D. and Barque, J.-P., *Gene expression of a protein JB70, related to rat $\alpha_1$-acid glycoprotein in Euglena gracilis, Biochem. Biophys. Res. Commun.,* 234, 544-548 (1997)].

AGP-like proteins are found in eukaryotes and the human AGP genes have been identified (AGP-A, AGP-B, and AGP-B). Thus, human AGP or an active derivative can be manufactured via known recombinant methods. In these methods, AGP or an active derivative can be expressed by inserting AGP genes into suitable cells or organisms, including single-cell and multi-cell organisms. Recombinant methods of manufacturing AGP are known in the art. One example of a method of manufacturing AGP via a recombinant method is described in Dente, L., Ruther, U., Tripodi, M., Wagner, E. F. and Cortese, R. *Expression of human $\alpha_1$-acid glycoprotein genes in cultured cells and in transgenic mice. Genes & Development*, 2, 259-266 (1988), which is hereby incorporated by reference. Such procedure could yield a sufficient amount of AGP or an active derivative to treat a large segment of diabetic population.

Comparisons of the effects of structurally different AGP molecules suggest that a smaller common sequence of the proteins is sufficient for the observed anti-diabetic effect. Biologically active derivatives of AGP containing less than 40 amino acids, and more particularly less than 25 amino acids, can be synthesized chemically for the therapeutic purpose described. Various methods of synthesis, such as solid phase peptide synthesis methods, are known in the art and may be used to synthesize active derivative(s) of AGP.

EXAMPLES

Comparative Example

Effects of $\alpha_1$-Anti-Trypsin (AT) and C-Reactive Protein (CRP) on the Level of Blood Glucose in Mice In this comparative example, the hyperglycemic effect of two acute phase proteins, AT and CRP, was shown. In each of these experiments the blood glucose level was measured 30 minutes after an administration of glucose (3 g/kg of body mass) via an intraperitoneal injection. Both proteins were administered to mice 24 hours prior to the glucose load. Mice were also starved for 16 hours prior to the glucose load. Mice that had received a 1.5 mg dose of human AT exhibited blood glucose levels of 8.1±0.40 mM while mice receiving no AT exhibited blood glucose levels of 7.35±0.45 mM, thus indicating a slight hyperglycemic effect of AT. The full spectrum of effects of AT on blood glucose levels have been revealed in another PCT application (International Patent Application No. PCT/US/2004/41508 titled "Method for improving insulin sensitivity by administering an inhibitor for administering an inhibitor of antitrypsin"); thus, the effect of AT will not be dealt with here in more detail.

In a second experiment, the effect of CRP on blood glucose level, both in the presence and absence of insulin, was measured in a usual glucose tolerance experiment. Mice that had received a 10 μg dose of CRP (24 hours prior to glucose load), and no dose of insulin, the blood glucose levels were 8.0±0.30 mM after 30 min of glucose load. In mice that had not received a dose of CRP (control) exhibited 6.80±0.40 mM of blood glucose levels. Mice that had received a 10 μg dose of CRP as well as a 0.25 I.U. dose of insulin injected intraperitoneally 15 min prior to glucose exhibited a blood glucose level of 2.50±0.45 mM. Mice that only received a 0.25 I.U. dose of insulin injected intraperitoneally 15 min prior to glucose and had not received a dose of CRP exhibited blood glucose levels of below 0.9 (low). Thus, CRP clearly had the tendency to enhance blood glucose levels both in the absence and presence of insulin, suggesting that it can partially desensitize glucose metabolizing organs, or at least one such organ, to the metabolic effects of insulin.

Description of Examples 1-3

In each example, C57/Black female mice, weighing 22-23 g each were each administered a tested agent via an intraperitoneal injection 2-24 hours prior to an administration of glucose (3 g/kg of body mass) via an intraperitoneal injection. All of the tested agents are available from Sigma-Aldrich, Inc. (St. Louis, Mo.). None of the animals received any food in addition to glucose for 16 hours prior to the administration of the glucose, or for the 3 hours following the administration of the glucose. At designated times after the administration of the glucose, blood samples were taken from the eyes (canthus), and glucose concentrations in whole blood samples were immediately measured with the fast Glucose C test, available from Wako Chemicals USA, Inc. (Richmond, Va.). The test does not accurately measure the glucose value below the 0.9 mM level and so levels below the 0.9 mM value are indicated as "low".

Example 1

Effect of Human AGP on Blood Glucose in Mice in the Absence and Presence of Insulin The time course of effects of 1 mg/mouse of human AGP on blood glucose levels was determined both in the absence and presence of insulin treatment. In each experiment, 1 mg/mouse human AGP and 0.25 I.U. insulin (Ins) were administered to mice 24 hours and 15 min, respectively, prior to a 3 g/kg of body mass glucose load. Blood samples for "0 min" were taken 5-10 min prior to the glucose load. Blood samples were also taken at 30, 60, 120 and 180 min after administration of glucose and analyzed. The results are shown in Table 1. Data are the mean ±S.D. of 4 determinations from four animals (one determination with each animal). In the untreated control animals, there was a sharp rise in the blood glucose level after 30 min of glucose injection, followed by a gradual decline. In the absence of insulin, AGP significantly decreased blood glucose level at each time point, with the largest difference being observed after 30 min. In the presence of insulin, the blood glucose level was too low to be accurately measured (indicated as "low") after 30 min. However, after 60 min insulin had practically no effect due to its rapid degradation. In the presence of insulin, AGP had a strong effect after 60 min as well as at later time points.

TABLE 1

AGP decreases blood glucose levels in mice during glucose tolerance test.

| | Blood glucose (mM) | | | | |
|---|---|---|---|---|---|
| Treatment | 0 min | 30 min | 60 min | 120 min | 180 min |
| None | 1.25 ± 0.15 | 7.00 ± 0.40 | 5.65 ± 0.45 | 4.40 ± 0.40 | 3.25 ± 0.30 |
| AGP | 1.10 ± 0.10 | 2.80 ± 0.55 | 3.00 ± 0.40 | 2.50 ± 0.20 | 2.10 ± 0.30 |

TABLE 1-continued

AGP decreases blood glucose levels in mice during glucose tolerance test.

| Treatment | Blood glucose (mM) | | | | |
|---|---|---|---|---|---|
| | 0 min | 30 min | 60 min | 120 min | 180 min |
| Ins | 1.25 ± 0.20 | low | 4.65 ± 0.40 | 3.90 ± 0.30 | 2.80 ± 0.35 |
| AGP + Ins | 1.25 ± 0.15 | low | 1.55 ± 0.40 | 3.70 ± 0.50 | 2.90 ± 0.30 |

Example 2

In Mice, Human AGP IS Equally Effective in Glucose Tolerance Tests when Administered 24 Hours or 2 Hours Prior to Administration of Glucose In another experiment, the time course of effects of 1.0 mg/mouse of human AGP on blood glucose levels was determined as before, except that in one experiment human AGP (hAGP) was added 24 hours prior to the 3 g/kg of body mass glucose load. While in another experiment, the hAGP was added 3 hours prior to the 3 g/kg of body mass glucose load. Blood samples were also taken at 30, 60, and 120 min after administration of glucose and analyzed. The results are shown in Table 2. Data are the mean ±S.D. of 6 determinations from six animals (one determination with each animal). As before, the untreated control animals experienced a sharp rise in the blood glucose level after 30 min of glucose injection, followed by a gradual decline. hAGP significantly decreased blood glucose level at each time point to similar extents regardless of whether the hAGP was administered 24 hours or 2 hours prior to the glucose load. This is indicates that the effect of AGP on blood glucose level is both relatively rapid and long-lasting.

TABLE 2

Comparison of timing of administration of AGP in mice.

| Treatment | Blood Glucose (mM) | | | |
|---|---|---|---|---|
| | 0 min | 30 min | 60 min | 120 min |
| None | 1.45 ± 0.35 | 7.85 ± 0.45 | 6.10 ± 0.30 | 3.00 ± 0.20 |
| hAGP, 24 hours | 1.60 ± 0.25 | 3.30 ± 0.40 | 2.60 ± 0.40 | 2.00 ± 0.50 |
| hAGP, 2 hours | 1.50 ± 0.30 | 3.60 ± 0.50 | 2.80 ± 0.20 | 2.40 ± 0.45 |

Example 3

Comparison of Various Concentrations of Human and Bovine AGP as well as Human Fibrinogen and Haptoglobin on Blood Glucose in Mice Next, the effects of different concentrations of human and bovine AGP proteins as well as high quality human fibrinogen (providing 90% clotting activity) and human haptoglobin on blood glucose level were compared. Human AGP (hAGP), bovine AGP (bAGP) and human fibrinogen were administered to mice, at the doses as indicated, 24 hours prior to administration of a 3 g/kg of body mass glucose load. Blood samples for "0 min" were taken 5-10 min prior to the glucose load. Blood samples were also taken at 30, 60, 120 and 180 min after administration of glucose and analyzed for glucose. The results obtained with AGP and fibrinogen (Fibrinog.) are shown in Table 3. Data are the mean ±S.D. of 4 determinations from four animals (one determination with each animal). Administration of AGP at the dose of 0.25 mg/mouse resulted in only slight reductions in the blood glucose level at the various time points. In contrast, administration of either human or bovine AGP at a dose of 0.6 mg/mouse resulted in significant, 50-42%, reduction in blood glucose at each time point examined. Human fibrinogen was about as effective as human or bovine AGP in reducing blood glucose. The results clearly indicate that (i) certain acute phase proteins, such as AGP and fibrinogen, actually reduce blood glucose, and that (ii) both human and bovine AGP is effective when administered at the dose of 0.6 mg/mouse.

In a separate experiment, the possible effect of the acute phase protein haptoglobin (0.5-0.8 mg/mouse) on blood glucose level was also examined; the same conditions that were used for the previous experiments were employed. Haptoglobin had effects neither in the absence nor in the presence of insulin (data not shown). Thus, haptoglobin is a representative of a group of acute phase proteins that do not alter blood glucose level.

TABLE 3

Comparison of different concentrations of human and bovine AGP as well as human fibrinogen on blood glucose in mice.

| Treatment | Blood Glucose (mM) | | | | |
|---|---|---|---|---|---|
| | 0 min | 30 min | 60 min | 120 min | 180 min |
| None | 1.20 ± 0.20 | 7.10 ± 0.40 | 5.60 ± 0.25 | 4.50 ± 0.30 | 3.50 ± 0.30 |
| hAGP, 0.25 mg | 1.10 ± 0.15 | 5.40 ± 0.30 | 4.80 ± 0.30 | 3.60 ± 0.30 | 2.90 ± 0.30 |
| bAGP, 0.25 mg | 1.05 ± 0.20 | 6.15 ± 0.25 | 5.00 ± 0.20 | 4.40 ± 0.20 | 3.40 ± 0.30 |
| hAGP, 0.6 mg | 1.00 ± 0.10 | 3.55 ± 0.30 | 3.25 ± 0.45 | 2.80 ± 0.50 | 2.35 ± 0.25 |
| bAGP, 0.6 mg | 1.15 ± 0.20 | 3.70 ± 0.15 | 3.15 ± 0.25 | 2.85 ± 0.30 | 2.35 ± 0.20 |
| Fibrinog. 0.6 mg | 1.15 ± 0.25 | 3.75 ± 0.35 | 3.35 ± 0.20 | 2.95 ± 0.25 | 2.50 ± 0.20 |
| Fibrinog. 1 mg | 1.10 ± 0.15 | 3.35 ± 0.45 | 2.90 ± 0.30 | 2.55 ± 0.45 | 2.15 ± 0.35 |

Example 4

Combined Effects of Human AGP and Human CP on Blood Glucose

Possible reversal of the hyperglycemic effect of ceruloplasmin (CP) by human AGP was examined. Since CP had similar, but longer-lasting, effects compared to CRP, CP was used as the model hyperglycemic acute phase protein to determine if the hyperglycemic effect of acutephase proteins may be countered by AGP. CP is a well known copper-binding protein with ferroxidase activity, mainly expressed and secreted by hepatocytes. Under normal conditions, extracellularly CP binds Fe(II), oxidizes it, and loads Fe(III) on to transferring. However, within intracellular compartments, CP-bound copper is readily made available for other Cu(II)-mediated reactions. It has not been reported that CP can modulate blood glucose level.

Human AGP (0.6 mg/mouse) and human CP (0.5 mg/mouse) were administered to mice 24 hours prior to a 3 g/kg of body mass glucose load. Blood samples for "0 min" were taken 5-10 min prior to the glucose load. Blood samples were also taken at 30, 60, 120 and 180 min after administration of glucose and analyzed for glucose subsequently. The results are shown in Table 4. Data are the mean ±S.D. of 4 determinations from four animals (one determination with each animal). At each time point examined, CP had the tendency to modestly enhance blood glucose values. This was particularly evident at the 60, 120, and 180 min time points. However, when AGP was present, the hyperglycemic effects of CP were diminished. In fact, in the presence of CP, AGP reduced blood glucose to about the same levels as when AGP was used alone (see Table 2). Based on these data, it is reasonable to expect that AGP also will be able to prevent the hyperglycemic effects of acute phase proteins that have such effects.

TABLE 4

AGP prevents CP-induced rise in blood glucose.

| Treatment | Blood Glucose (mM) | | | | |
|---|---|---|---|---|---|
| | 0 min | 30 min | 60 min | 120 min | 180 min |
| None | 1.30 ± 0.30 | 7.15 ± 0.35 | 5.75 ± 0.50 | 4.30 ± 0.40 | 3.15 ± 0.20 |
| CP | 1.20 ± 0.25 | 7.50 ± 0.30 | 6.95 ± 0.45 | 5.10 ± 0.35 | 3.95 ± 0.25 |
| CP + hAGP | 1.30 ± 0.35 | 3.90 ± 0.40 | 3.25 ± 0.35 | 3.00 ± 0.15 | 2.55 ± 0.30 |

Description of Examples 5-6

In examples 5-6, the effects of AGP on blood glucose level and weight in mice with STZ-induced Type 1 diabetes were measured. Six BDF-1 male mice, each weighing about 27-28 g, were first administered 1.2 mg/mouse of Sigma hAGP via intraperitoneal injection. This administration occurred on Day −1. Twenty four hours later on Day 0, twelve BDF-1 mice, including the six treated with hAGP, were treated once with streptozotocin (STZ) at a dose of 200 mg/kg. This dose of STZ is widely used to selectively destroy insulin-producing β cells in the islet by an oxidative mechanism thus inducing Type 1 diabetes. Animals in the STZ+AGP subgroup were repeatedly treated with hAGP at a dose of 1.2 mg/mouse of hAGP on Days 2 and 5. An additional group of 6 BDF-1 male mice were not treated with any agent. Blood glucose (collected from the retina) and body weight was measured on days −1, 0, 2, 5, 7, 9, and 11.

Example 5 hAGP Prevents Large Increases in Blood Glucose in Mice with STZ-Induced Type 1 Diabetes The data presented in Table 5 shows the effect of HAGP on blood glucose in mice with STZ-induced Type 1 diabetes. In the first column, the blood glucose level of control mice (i.e. those not given STZ to induce Type 1 diabetes or AGP) is presented. The second column provides data on mice that were given STZ to induce Type 1 diabetes, but were not given AGP. The Third column provides data on mice that were given both STZ to induce Type 1 diabetes and AGP. Data are the mean ±S.D. of 6 determinations from six animals (one determination with each animal). The control mice maintained their normal range of blood glucose level during the whole experimental period. In mice given STZ only, the blood glucose level rose continuously, approaching nearly a 400% increase by day 9. The mice treated with both STZ and hAGP-treated experienced only a two-fold increase in blood glucose level after 11 days, even though treatment with AGP was stopped after 5 days. This experiment indicated that hAGP can exert a significant and long-term lowering effect on blood glucose level in this widely used animal model of Type 1 diabetes. Thus, treatment with hAGP is likely to exert similar effects in humans afflicted with Type 1 diabetes.

TABLE 5 hAGP reduces STZ-induced large increase in blood glucose in mice.

| Day | Blood Glucose (mM) | | |
|---|---|---|---|
| | Control | STZ | STZ + hAGP |
| −1 | 3.95 ± 0.35 | 4.10 ± 0.60 | 4.20 ± 0.30 |
| 0 | 4.00 ± 0.30 | 4.05 ± 0.50 | 3.20 ± 0.20 |
| 2 | 3.90 ± 0.40 | 12.2 ± 1.60 | 9.40 ± 0.50 |
| 5 | 3.90 ± 0.45 | 16.5 ± 1.30 | 8.90 ± 0.30 |
| 7 | 4.10 ± 0.20 | 18.6 ± 1.00 | 8.30 ± 0.35 |
| 9 | 3.80 ± 0.30 | 19.5 ± 0.60 | 7.90 ± 0.40 |
| 11 | 4.05 ± 0.20 | 19.8 ± 0.80 | 8.00 ± 0.45 |

Example 6 hAGP Prevents Loss of Body Weight in Mice with STZ-Induced Type 1 Diabetes

The body weight of the mice described in Example 5 was also regularly measured. The data, presented in Table 6, are the mean ±S.D. of 6 determinations from six animals (one determination with each animal). The control mice gained about 3 g during the 12 days examination period while the mice with STZ-induced Type 1 diabetes and no hAGP lost 8.1 g. Mice with STZ-induced Type 1 diabetes that were treated with hAGP exhibited less weight loss than mice with STZ-induced Type 1 diabetes that were not treated with hAGP.

TABLE 6 hAGP prevents STZ-induced loss of body weight in mice.

| | Body weight (g) | | |
| --- | --- | --- | --- |
| Day | Untreated (Control) | STZ | STZ + hAGP |
| −1 | 27.5 ± 0.50 | 28.7 ± 0.45 | 28.2 ± 0.50 |
| 0 | 27.3 ± 0.60 | 28.5 ± 0.40 | 28.4 ± 0.70 |
| 2 | 28.4 ± 0.75 | 24.7 ± 0.40 | 26.9 ± 0.55 |
| 5 | 28.9 ± 0.60 | 22.5 ± 0.60 | 27.1 ± 0.50 |
| 7 | 29.3 ± 0.65 | 21.2 ± 0.55 | 28.2 ± 0.45 |
| 9 | 29.5 ± 0.75 | 20.9 ± 0.35 | 28.9 ± 0.60 |
| 11 | 30.6 ± 0.85 | 20.6 ± 0.50 | 29.1 ± 0.70 |

Example 7 hAGP Reduces Blood Glucose Level in Glucose Tolerance Test in Rats

Male Wister rats, kept on standard diet and weighing 250-300 g, were used to show that the effect of hAGP on reducing blood glucose level in glucose tolerance tests is not restricted to mice. Sigma hAGP (12mg/rat) was administered to 10 rats 24 hours prior to a 3 g/kg of body mass glucose load. 10 control rats remained. All animals were deprived of food for 16 hours prior to the glucose load and for 5 hours following the glucose load. Blood samples were taken from the tail vein a few minutes prior to administering glucose (0 min) and then also 30, 60, and 120 min after the rats were given a standard glucose load. The data, presented in Table 7, are the mean ±S.E. of 10 determinations from 10 animals (one determination with each animal). Pre-treatment of rats with hAGP for 24 hours appeared to only slightly decrease blood glucose level slightly prior to the glucose load (i.e. at 0 time in Table 7), indicating that this protein does not cause hypoglycemia in rats. In contrast, after 30 min of administering glucose, the level of blood glucose in hAGP-treated rats was 12.7 mM compared to 17.2 mM in the control rats.

| | Blood Glucose (mM) | | | |
| --- | --- | --- | --- | --- |
| Treatment | 0 min | 30 min | 60 min | 120 min |
| None | 7.05 ± 0.30 | 17.20 ± 0.95 | 14.30 ± 0.90 | 9.90 ± 0.50 |
| hAGP | 6.20 ± 0.35 | 12.70 ± 0.90 | 12.65 ± 1.20 | 8.60 ± 0.50 |

The invention claimed is:

1. A method of reducing blood glucose level, comprising the step of administering to a mammal in thereof a therapeutically effective amount of α1-acid glycoprotein.

2. The method of claim 1 wherein the mammal has an above-normal blood glucose level before administration of $\alpha_1$-acid glycoprotein.

3. The method of claim 2 wherein administration of $\alpha_1$-acid glycoprotein is effective to reduce the mammal's blood glucose level to within the range of about 4-6 mM.

4. The method of claim 1 wherein the mammal is afflicted with Type 1 diabetes or Type 2 diabetes.

5. The method of claim 4 wherein the method further comprises administering an anti-diabetic medicament in combination with $\alpha_1$-acid glycoprotein.

6. The method of claim 5 wherein the anti-diabetic medicament comprises one of an insulin secretogogue, a biguanide, an inhibitor of α-glucosidase, a thiazolidinedione, or NN2211.

7. The method of claim 5 wherein the anti-diabetic medicament comprises insulin.

8. The method of claim 1 wherein the $\alpha_1$-acid glycoprotein is administered prior to an expected glucose load.

9. The method of claim 1 wherein the mammal is a human.

10. A method of treating diabetes, comprising periodically administering to a human in need thereof a therapeutically effective amount of α1-acid glycoprotein.

11. The method of claim 10 wherein the treatment regimen further comprises administering an anti-diabetic medicament in combination with the $\alpha_1$-acid glycoprotein.

12. The method of claim 10 wherein the therapeutically effective amount is in the range of about 0.1-4.0 g per 100 kg of the human's body mass.

13. The method of claim 10 wherein periodic administration of $\alpha_1$-acid glycoprotein is effective to maintain the human's blood glucose level within the range of about 4-6 mM.

14. The method of claim 1 wherein the therapeutically effective amount is in the range of about 0.1-4.0 g per 100 kg of the mammal's body mass.

* * * * *